United States Patent [19]

Hill

[11] 3,946,110

[45] Mar. 23, 1976

[54] MEDICINAL COMPOSITIONS AND METHODS OF PREPARING THE SAME

[75] Inventor: William H. Hill, St. Paul, Minn.

[73] Assignee: Peter, Strong Research and Development Company, Inc., Port Chester, N.Y.

[22] Filed: Feb. 10, 1975

[21] Appl. No.: 548,540

Related U.S. Application Data

[63] Continuation of Ser. No. 474,599, May 30, 1974, abandoned, which is a continuation of Ser. No. 277,900, Aug. 4, 1972, abandoned, which is a continuation of Ser. No. 863,053, Oct. 2, 1969, abandoned.

[52] U.S. Cl............................ 424/230; 424/361
[51] Int. Cl.² .................... A61J 3/10; A61K 9/20
[58] Field of Search............................ 424/230, 361

[56] References Cited
UNITED STATES PATENTS

| | | | |
|---|---|---|---|
| 2,798,838 | 7/1957 | Robinson | 424/34 |
| 2,887,436 | 5/1959 | Klioze et al. | 424/280 X |
| 2,887,437 | 5/1959 | Klioze et al. | 424/280 X |
| 2,887,439 | 5/1959 | Klioze et al. | 424/280 X |
| 3,065,143 | 11/1962 | Christenson et al. | 424/19 |
| 3,079,303 | 2/1963 | Raff et al. | 424/35 X |
| 3,266,992 | 8/1966 | deJong | 424/280 X |
| 3,424,842 | 1/1969 | Nurnberg | 424/227 X |
| 3,427,378 | 2/1969 | Henderson et al. | 424/14 |
| 3,444,290 | 5/1969 | Wai | 424/37 X |
| 3,485,920 | 12/1969 | Bender | 424/361 X |

*Primary Examiner*—Shep K. Rose

[57] ABSTRACT

Improvements are set forth in connection with analgesic and antifebritic or antipyretic compositions, tablets with solid medicaments, and methods of preparing such compositions and tablets. Medicament particles, such as aspirin particles, for instance, and pectin or gum particles are included as main constituents in mixtures in which the pectin or gum serves to prevent undesirable side effects and in which coated and uncoated or exposed surfaces of medicament, or specifically aspirin, particles can be proportionately varied to vary or extend periods of medicinal activity of the medicament, or aspirin. In the methods of preparation, water can be included with or without water carriers and proportioned in a mix to soften the pectin or gum while maintaining the mix in a pourable state. On compression, a mix can be readily formed into tablets.

8 Claims, 4 Drawing Figures

MEDICINAL COMPOSITIONS AND METHODS OF PREPARING THE SAME

This is a continuation of application Ser. No. 474,599 filed May 30, 1974, now abandoned which is a continuation of application Ser. No. 277,900 filed Aug. 4, 1972 now abandoned which in turn is a continuation of application Ser. No. 836,053 filed Oct. 2, 1969 now abandoned.

The present invention relates to improvements in analgesic and antifebritic or antipyretic compositions, improvements in tablets containing solid medicaments, and in methods of preparing such compositions and tablets.

One of the most widely known among pharmaceuticals for use as an analgesic, antipyretic or antirheumatic is acetylsalicylic acid, referred to as aspirin. It is well known that attempts have been made to improve and prolong its action and to eliminate certain undesirable side effects. Stomach pains and nausea have been found to occur from rubbing or resting of aspirin tablets on the mucosa of the stomach, particularly when empty. Bleeding may also be brought on by such contact of the stomach mucosa with aspirin. Blood losses have been known to be very substantial and have actually led to anemia conditions. The presence of blood is frequently observed in the stools of arthritics and others taking large doses of aspirin.

To overcome at least some of the undesirable side effects, acetylsalicylic acid has been prepared and administered in the form of its sodium salt. This is unstable, and must be freshly prepared when administered. It cannot satisfactorily be embodied in a preparation purchased in a drugstore and kept on hand by a patient. Its use, for this reason, is substantially restricted to administration by physicians and nurses who prepare it when ready to be administered. Another approach is the inclusion of butters, such as amino acids, for example, glycine, which supposedly counteract the acidity of aspirin. Such use of buffers is, in effect, quite illusory, since the stomach contains 0.2 to 0.4% or the equivalent of about 1/10 normal hydrochloric acid.

As one expedient, manufacturers have fine-ground acetylsalicylic acid, and compounded it into tablets in such manner that rapid disintegration takes place in the stomach. This is apparently, at best, a palliative in that it tends to prevent too severe local irritation and perhaps prevents hemorrhaging since no large particles of a tablet contact the stomach mucosa. It does not overcome the effects of very poor water solubility of acetylsalicylic acid. The acetylsalicylic acid is merely dispersed in the stomach contents in the form of fine, discrete particles. The local irritating effect of such solid particles is not satisfactorily overcome. Moreover, the characteristics of ordinary aspirin tablets tend to bring about a relatively fast rise of the blood level of salicylic acid, and, therefore, fast and massive relief, but also a rather rapid dissipation of pain-relieving effects whereafter a need for renewed medication becomes soon apparent.

It has now been discovered that tablets containing solid medicaments, such as aspirin and others, can be produced with greatly improved characteristics by compounding them with natural, water-swellable gums, preferably those having a poly-uronic acid molecular structure, such as pectins and alginates of various origins, tragacanth, karaya, and other gums such as carrageenin. It is noted that when aspirin tablets, containing such gums or natural plant hydrocolloids and particles of acetylsalicylic acid, enter the stomach, the aspirin particles, particularly when a hydrocolloid surrounds or coats separate, fine aspirin particles of a tablet, do not have the aforesaid undesirable effects. The surrounding hydrocolloid swells with the moisture of the stomach to a gel which effectively prevents direct contact of said particles with the stomach mucosa. However, the particles of the medicament can dissolve gradually, because moisture diffuses into or penetrates and passes freely through the gel which serves in effect as a semi-permeable membrane. The acetylsalicylic acid solution that forms within a gel-coated particle and passes outwardly through a gel mass or coating mixes with gastric juice in the stomach and eventually is absorbed into the blood and is circulated, relieving pain, reducing fever, or diminishing other undesirable conditions.

Many different effects can be achieved by compounding polyuronic acid gums with acetylsalicylic acid in various manners, for instance, by varying the proportions of coated and uncoated particles in a tablet or a powder, and by varying the thickness of a coating on the particles of aspirin. If every particle of aspirin in a tablet or powder is completely or at least partially coated with such a gum, the pain and fever-relieving effects will progress more slowly and will last longer than with a less extensive coating or than with no coating. If the coating is a heavy or a relatively thick one, the effect of the medicament will be delayed longer than if the coating is a thinner one. Further modifications of the effects of acetylsalicylic acid can be obtained by using low methoxyl pectins as distinct from ordinary pectin or high methoxyl pectin or by varying the proportions of these with respect to that of aspirin or with respect to each other. The setting of low methoxyl pectins is more rapid in the presence of polyvalent cations, such as calcium ions. Coatings of a low methoxyl pectin on particles of aspirin and coatings affected by the calcium ions are harder and firmer than, and swell less than those obtained with ordinary pectin, and acetylsalicylic acid solution diffuses through such coatings with greater difficulty or at lower rates. The alginates behave somewhat similarly to the low methoxyl pectins in that they are also sensitive to polyvalent cations, such as calcium ions. Calcium ions are known to be present in saliva and in gastric juice at all times, so that some setting of the gel films surrounding the particles of acetylsalicylic acid in a tablet or powder can occur readily under the conditions of use of such tablets or powders. Setting may be accelerated by incorporating calcium salts, or other polyvalent metal salts, with particles of acetylalicylic acid before coating them with the gum. Calcium citrate is a preferred salt for this purpose, but calcium carbonate, calcium sulfate, magnesium carbonate, aluminum hydrate, and other such compounds are likewise useful for the purpose. Water-soluble salts of polyvalent metals, such as calcium chloride, calcium gluconate, magnesium sulfate, ferrous sulfate, and others are best incorporated during a tableting operation, and after the particles of acetylsalicylic acid have been gum-coated.

Mixes of particles of natural plant hydrocolloids and individual particles of solid medicament coated completely or partially with a natural plant hydrocolloid, are noted as products. Mixes are also noted which contain uncoated particles of a solid medicament, and solid particles of the medicament which are coated as described above with a pectin, or alginate, or carrageenin, as such, or modified as indicated. In the latter mixes, the coated and uncoated medicament are proportioned to provide initial immediate release of a predetermined quantity of a medicament in an administered dose, and a subsequent release of a predetermined quantity of the medicament at a predetermined rate and over a predetermined period of time. Tablets prepared with the aforesaid mixes are noted.

In preparations such as those referred to above, mixes are also provided in which medicament or drug particles are at least partially, or partially to completely submerged in the surfaces of the solid particles of pectin, or algin, or carrageenin. This is accomplished by softening the outer surfaces of the hydrocolloid particles with water, as noted hereinbelow, and mixing the medicament or drug particles, such as an aspirin powder, with the presoftened hydrocolloid particles. Sharp edges of crystals of medicaments or drugs become embedded in such particles, or granules, of hydrocolloid. Softening is carried out by direct application of moisture or by means of a so-called water-carrier or water-absorbing material, referred to below, which is a medically inert, finely divided solid, capable of absorbing water. The water carrier is pretreated or prewetted with water in amount which is normally sufficient merely to soften the surface or a thin outer layer or zone of a particle of the hydrocolloid. Water for this purpose may be used preferably to the extent of approximately between 2% and 12% by weight of a total mix in a tablet. This range depends on the "natural" moisture content of hydrocolloid gums, which, as sold may vary anywhere from 5 to 15% and more usually from about 8 to about 12%. Conditions of manufacture, handling and storage of such hydrocolloids also affect their moisture content.

The water carrier serves not only as a means for transferring moisture to soften the surfaces of the hydrocolloid particles without clumping, but also, particularly in tablets, for increasing the speed of disintegration or of release of a medicament in that the carrier permits easy entrance and penetration of water or digestive juices contacted on administration.

It appears that when aspirin crystalline particles are embedded in a hydrocolloid, the particles are subdivided into smaller particles and each of such smaller particles is ultimately surrounded by the hydrocolloid. Thus there results a distribution of fine particles of aspirin in a hydrocolloid particle. Fine particles of aspirin, even microscopic in size, and distributed in a granule of hydrocolloid provide for greater control over the effects of the aspirin and over the uniformity and magnitude of the release of aspirin.

Aspirin tablets are prepared as herein prescribed to provide not only means to bring about disintegration of a tablet in digestive juices but means that serve to control the release of a medicament from a tablet mix. The disintegration is preferably relatively rapid and into particles with a sufficient coating that furnishes effective protection for the mucosa of the stomach and yet is not an impenetrable barrier to the digestive juices that dissolve a medicament. Aspirin tablets are prepared primarily as multi-component, delayed action tablets. For this purpose and for the control of such action some particles of acetylsalicylic acid pre-prepared for tableting may be, if desired, coated with pectins and others with alginates, or carrageenin, some with heavy layers of these coatings and others with light or thin layers, some with high-methoxyl pectins and others with low-methoxyl pectins, some with sodium or potassium alginates and others with alginic acid or esters thereof, and as indicated above, some with additions of salts of polyvalent metal cations and others without such additions. Combinations of any two or more of these coating agents are noted.

For improved effects, particularly in the rapidity of disintegration, in a desired so-called mushrooming of a gel structure containing particles of a medicament, and in the proper control of the rate of release, it is generally preferred not to provide an outer coating of a gum on a tablet. Such outer coating tends to prevent rapid disintegration of a tablet unless it is carefully chosen. Particles of a medicament in a tablet are preferably individually coated. However, when tablets are prepared from an intermixture of uncoated medicament particles and gum particles, the medicament particles and gum particles must preferably be in juxtaposition. The gum particles in a tablet preferably surround substantially each medicament particle, and are side by side and in contact with the latter.

The gums, such as pectins, alginates, and carrageenin, used in achieving the objectives of the present invention, and especially the pectins, besides functioning in the coatings as gel-type barriers through which a medicament diffuses in the stomach, serve as hemostyptics. When used in accordance with this invention, they counteract any tendency of the acetylsalicylic acid to cause hemorrhaging in the stomach or intestines, and they serve to stop bleeding if it occurs. Pectin and, it is believed other gums, serve to prolong the action of medicaments in the human body, and also to solubilize them.

Pectins and alginates are natural plant hydrocolloids comprising mainly polyuronic acids, and when compounded with acetylsalicylic acid they introduce no element of danger of undesirable side effects in an otherwise desirable therapy. They are not body-alien but are considered non-assimilable. The exact mechanisms are not too well understood. However, pectin, for example, is believed to be de-methoxylated by enzymatic action, as by pectinase, and by acid hydrolysis in the stomach, as well as by alkaline hydrolysis in the intestines. No adverse effects have been noted. Pectins constitute appreciable proportions of edible fruits and vegetables, including apples and citrus fruits, and plant life in general, from which they have been isolated and found to be harmless.

Plant hydrocolloids vary in character, depending upon their source and methods of production. Wettability, for instance, of particles of these gums depends to a great extent upon modes of recovery or upon treatments employed in the preparation of them as by heating and flaking. It is preferred to employ gum particles in the process of the present invention, which are wettable.

In the production of combinations of acetylsalicylic acid with plant hydrocolloids, such as pectins, alginates, and carrageenin, it has been found that some water is required for best results. For instance, a mixture of pectin and acetylsalicylic acid, both in powdered form (both about 80 mesh), is introduced into enough water to permit granulation and to permit passage of the moist mass through screens with openings of a desired size, for example, 16 to 30 mesh. After granulation, the granulated material is rapidly dried at room temperature (60° to 80° F.) or at slightly higher temperatures (80° to 90° F.) to prevent substantial hydrolysis of the acetylsalicylic acid. The use of a vacuum in this drying process is helpful but not essential. Granulation is also carried out by adding water in the form of a fine spray or mist to a mixture of plant hydrocolloid and acetylsalicylic acid while the mixture is vigorously agitated. Because of the fact that in either method of granulation the particles of plant hydrocolloid are intimately commingled with particles of acetylsalicylic acid, severe lumping is avoided, whereas considerable lumping does occur when plant hydrocolloids, such as pectins, alginates, and carrageenin, alone are mixed with water. These methods are distinctly advantageous and serve considerably to facilitate the manufacturing process.

The lumping referred to above can be reduced and substantially eliminated by adding to an original mixture of plant hydrocolloid and acetylsalicylic acid up to 10% of its weight of water-absorbing materials such as starches, clays, silica gel, and especially finely divided siliceous materials such as a silicon dioxide known as "Cab-O-Sil". "Cab-O-Sil" (made by Godfrey L. Cabot, Inc.) is a colloidal, submicronic or submicroscopic, pyrogenic silica prepared in a hot, gaseous environment by a vapor-phase, flame hydrolysis, at high temperature (1100° C.), of a silicon compound, such as silicon tetrachloride. It is distinct from silica gel obtained by precipitating silicic acid from an aqueous silicate solution, and hardening of the precipitate. Silica gel, thus formed, is internally porous. "Cab-O-Sil" has enormous external surface area and no internal porosity and contains no water-soluble inorganic salts. It is of high chemical purity, low water content, a high degree of particle separation, and the particles are almost spherical in shape. One grade (designated as M-5) of "Cab-O-Sil" has a particle size range of 0.015 to 0.020 micron, and a surface area of substantially 175 to 200 square meters per gram. A finer grade (hereinbelow designated as H-5) has a particle size range of 0.007 to 0.010 micron, and a surface area of substantially 325 square meters per gram.

Of the various starches that are procurable in the trade and that are useful in this process, there may be mentioned corn starch, potato starch, wheat starch, rice starch, tapioca starch and such specialties as high amylose starch and high amylo-pectin starch. In general, potato starch is preferred.

By including a water-absorbing material and uniformly distributing it in the mix, there results a more uniform pick-up of water by the hydrocolloid. The mix is prevented from forming a gel, and from becoming a paste, or gummy, or a slurry. The water-absorptive material is pharmaceutically acceptable. "Cab-O-Sil", in particular, is highly absorptive, of high purity, and is completely innocuous.

Water-absorbing materials, such as the above, absorb water as it comes in contact with the mixture to be granulated, and thus prevents lumping, whereafter the water is yielded gradually to the plant hydrocolloid, thus permitting the latter the hydrate and swell gradually. Mixtures thus prepared with plant hydrocolloids and acetylsalicylic acid containing up to substantially 10% of added water do not appear moist and are pourable or "free-running". As noted hereinbelow they are advantageously useful in tableting.

Besides the above methods by which mixtures are prepared in which particles of plant hydrocolloid are in close juxtaposition to and surround particles of acetylsalicylic acid, another method is used particularly for assuring complete coating of all particles of acetylsalicylic acid with a layer of plant hydrocolloid. According to this method, the acetylsalicylic acid required in a formulation is mixed intimately with a portion of the selected natural plant hydrocolloid, as for example, pectin. This mixture is added to water, with thorough stirring, until a somewhat slimy but grainy slurry is obtained. Because acetylsalicylic acid in water is ionized, presence of the acid prevents effectively any tendency of the pectin component to lump and gel in this operation to a solid mass, and the resulting slurry or paste is very homogeneous and grainy in appearance, and only moderately sticky. The remaining portion of the prescribed amount of pectin is now gradually added to the slurry, or paste; or the slurry or paste is added to the said remaining portion of pectin. Soft lumps formed in the latter mixing operation are gradually broken up in continually renewing contact between them and drier portions of the mixture by intensive mixing or rubbing. Differential speed rolls are helpful in tearing apart the lumps and incorporating dry pectin in them. The final product may be dried to a stage where it can be passed through screens of desirable mesh, such as 30 to 40 mesh.

When attempting to coat aspirin particles, or other medicaments, with pectin or other hydrocolloids a great deal of difficulty is experienced in a wet granulation process because pectin with water swells and forms extremely thick and viscous solutions and even solid gels at concentrations above about 2% pectin in water. It is difficult to mix such viscous solutions or gels with, for instance, aspirin crystals in such a manner that all crystals are coated with the pectin solution or gel. It has been discovered that the difficulties normally encountered can be greatly alleviated and even eliminated if, to begin with, only a very small amount of pectin is mixed with a very large excess of aspirin such as, for instance, in a ratio of 10% pectin and 90% aspirin. When a mixture of the two components in approximately this ratio is introduced into water the aspirin ionizes and prevents the formation of viscous pectin solutions or gels. Instead, relatively easy flowing grainy slurries are obtained which carry the aspirin particles completely coated with pectin. In further processing such a granulation, additional increments of pectin are added and the mass being processed gradually becomes much more viscous and even somewhat rubbery. However, since the aspirin particles were coated in the beginning, there is now no more danger of having uncoated aspirin particles in the final mix because of difficulties in handling the more viscous solution, and gel-like masses obtained after the addition of further increments of pectin. The pectin added in such later increments substantially behaves as an inert with which the initial pectin coated aspirin grains or crystals are mixed.

Granular or powdered mixes of solid medicaments and solid plant hydrocolloids are illustrated diagrammatically in the accompanying enlarged figures in the drawing in which:

Figure 1:
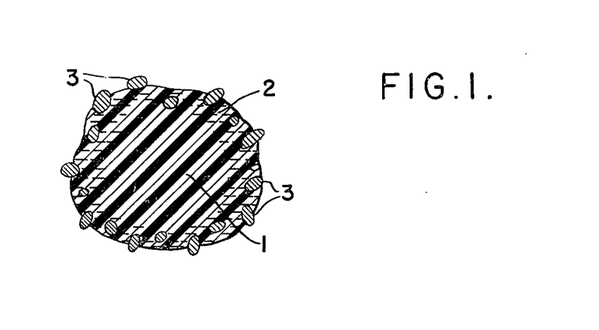

FIG. 1 is an enlargement of a cross section of a hydrocolloid granule 1 an outer layer 2 of which is in a softened state. In this outer layer, granules 3 of a medicament such as aspirin, are partially or completely embedded. The medicament particles are smaller in size than the hydrocolloid particles, and may be microscopic in size. In administering preparations, the exposed portions of the medicament particles are released and utilized substantially immediately, and the submerged portions are delayed in their action whereby the period of effectiveness is extended. The period is varied depending upon the proportionate extent of submergence of the medicament particles in hydrocolloid particles as well as the proportion of medicament in the preparation.

Figures 2, 3:
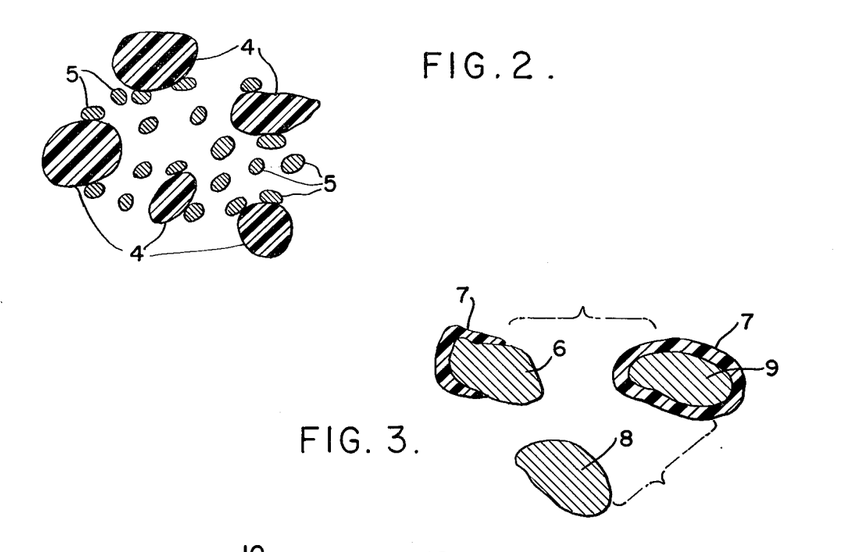

FIG. 2 is an enlargement of a mix in which are shown hydrocolloid particles 4 surrounding particles 5 of solid medicament. Particles 5 of medicament may adhere to the outer surfaces of the hydrocolloid particles 4. Particles 5 in excess of adhering particles tend to maintain the mix pourable. These can be varied in size and in proportion.

FIG. 3 serves to illustrate a pourable solid mix in which particles 6 of a medicament are at least partially coated with a hydrocolloid 7, shown in section, and uncoated medicament particles 8, in section. Some particles of medicament such as particle 9 may be completely coated. Proportions of these various particles may vary to provide the desired timing. Also the coating may vary in thickness and composition. Low methoxyl pectin or high methoxyl pectin, or other hydrocolloids may be used as coatings depending on the desired timing.

Figure 4:
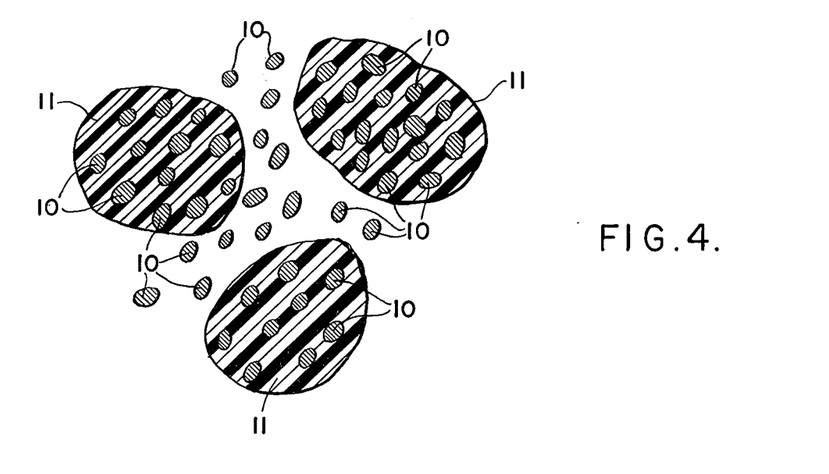

FIG. 4 illustrates a preparation in which very small and even microscopic sized particles 10 of medicament (enlarged section) are distributed throughout the body of a hydrocolloid particle 11 (section) in a pourable mix. A certain proportion of medicament particles may be surrounded by such hydrocolloid particles 11, and different hydrocolloids may be used depending on the desired timing of release.

Still another method of the present invention avoids what is understood to be wet granulation, and can be particularly included in a tableting procedure. It comprises adding water to the aforesaid water-absorbing materials or a water carrier, preferably medically inert (starches, "Cab-O-Sil", or mixtures thereof), in such proportions that the moisturized material continues to appear dry and is pourable or free-flowing; mixing this moisturized material intimately with appropriate proportions of acetylsalicyclic acid and plant hydrocolloid; placing the resulting mix in a closed container for about 1 to 24 hours to permit more or less equal distribution of the water by isothermal distillation, throughout the mix; tableting the resultant product, and drying the final tablets. The temperature at which the isothermal distillation is carried out is not critical; normally it can be conducted at ambient room temperature or at a temperature somewhat above or below ambient temperature and even in a refrigerator or freezer. The reduced temperatures are particularly advantageous where hydrolysis of the medicament, such as acetylsalicylic acid, is of concern and is to be avoided.

In some cases it is desirable to precede the actual tableting operation by a preliminary "slugging" step in which the mix is lightly compressed; breaking up the slugs to a desired grain size; and finally compressing to form the desired tablets. In this latter method, it has been found preferable to employ the plant hydrocolloid and the acetylsalicylic acid in similar grain sizes to avoid segregation in a mix, but for most purposes this is not essential. Acetylsalicylic acid is used as a 40-mesh crystal as well as an 80-mesh USP powder, with a plant hydrocolloid such as pure citrus pectin of about 80 mesh and finer, and also as a mixture of 40-mesh crystal and 80-mesh powder. Any other desirable mesh size of medicament and hydrocolloid may be used.

Other medicaments are noted for inclusion in the tablets and in mixtures of aspirin and plant hydrocolloid, as for example, acetophenetidine, caffeine and others.

Aside from administering combinations of acetylsalicylic acid and plant hydrocolloids in mixes in powdered, capsule, or tablet form, the tableting of such mixes by particular methods is noted. It is well known that tablets for medical use are made by various methods, including those referred to as (1) direct compression, (2) granulation by the precompression or "slug" method, and (3) wet granulation. In such methods, it has heretofore been the practice to perform the tableting step in a tableting machine after a mix is thoroughly dried. The presence of water during such step was thought to cause sticking of mixes to the punches and dies, and was considered a serious hindrance to the proper formation of tablets.

In the formation of tablets in processes herein disclosed, the presence of water in mixes for tableting is found to be highly important. In a procedure for granulation for instance, a mixture of pectin and acetylsalicylic acid, both in powdered form, for example, both about 80 mesh, is introduced into enough water to permit granulation and to permit passage of the moist mass through screens with openings of a desired size, for example, 16 or 30 mesh. After granulation, the granulated material is rapidly dried at room temperatures or slightly above to prevent substantial hydrolysis of the acetylsalicylic acid. The use of a vacuum in this drying process is helpful but not essential.

The following examples are included for purposes of illustration:

EXAMPLE 1

| | |
|---|---|
| Acetylsalicylic acid, 80 mesh powder | 80 grams |
| Citrus pectin, pure, 220 US grade | 20 grams |

The above ingredients were intimately and thoroughly mixed. Attempts to compress the mixture into tablets in a single punch press failed. Broken tablets were produced, and the pieces were crushed and passed through screens to provide a 20 to 60 mesh fraction. This fraction could not be compressed into satisfactory tablets. The fines from the second screening plus the 20 to 60 mesh fraction were brought together to provide the original 100 gram mixture, and 1 gram of "Cab-O-Sil", the M-5 grade, was thoroughly mixed therewith. Satisfactory tablets could not be produced with this mixture. The material was crushed and screened through a 20-mesh screen and carefully wetted with successive small amounts of water with constant stirring. The larger aggregates which formed upon each addition of water were broken up. There was no gumminess, and the aggregates were broken up and dispersed without difficulty. The granulated material was placed in an oven at about 55° C. for about fourteen hours to remove moisture. Tableting of this material was not successful. The moisture content in the granules was still too high and the material stuck to the die. The material was broken up as much as possible and placed in the oven at about 85° C. for about 4 to 6 hours. The resulting mix was compressed into fairly satisfactory tablets. With addition of 1% by weight of stearyl alcohol as a lubricant, fairly good tablets were produced having a weight of 0.6 gram. When dropped into water, the tablets swelled immediately and then broke up into a slurry.

EXAMPLE 2

| Aspirin-starch granulation (ninety parts aspirin, ten parts starch, by weight) 12/50 mesh | 100 grams |
|---|---|
| Citrus pectin, pure, 220 US grade | 100 grams |

These ingredients were thoroughly mixed and compressed directly into tablets. The tablets (weight 0.46 gram) were not too good. They disintegrated in water in 5 to 10 seconds and a jelly-like mass was formed by each.

EXAMPLE 3

| Acetylsalicylic acid USP, 80 mesh powder | 50 grams |
|---|---|
| Citrus pectin, pure, 220 US grade | 50 grams |

These ingredients were thoroughly mixed. The mixture was spread out on a polyethylene sheet, and water, in small increments was sprayed with a fine spray onto the spread mix. A total of 14 grams of distilled water was thus applied. The mix was turned over with a spatula after each addition of water. The resulting mixture was placed in a drying oven at low temperature, in this instance at 52° C. The final weight of the mix was 96 grams. The weight loss includes the evaporated water and the losses incurred in handling and transferring the mix. It appeared that a considerable portion of the added water had evaporated. Direct compression of this mix yielded tablets (weight per tablet, 0.47 gram) that were firm but not hard. When added to water, a tablet swelled to a mass with a vertical height of about three-fourth inch, and a horizontal diameter of about one-half inch. The mass had the appearance of a large mushroom, and was very fluffy but coherent.

EXAMPLE 4

1550 grams of 40 mesh acetylsalicylic acid USP were hot-coated by the well-known Wurster process with a 1% aqueous solution of Italian citrus pectin (240 US grade, fast set) containing a total of 5 grams of pectin to coat the particles of acetylsalicylic acid. About 100 grams of the resulting material was compressed directly into tablets (weight per tablet, 0.5 gram) of good appearance.

Another lot of the pectin-coated acetylsalicylic acid particles was mixed with 1% by weight of magnesium stearate. This mix was easily compressed to produce tablets (weight per tablet, 0.5 gram) that were glossy and of very good appearance.

A third lot of the pectin-coated acetylsalicylic acid particles was mixed with additional Italian citrus pectin (240 US grade, slow set) in the ratio of 75% by weight of said particles to 25% of the pectin. On compression, this mix produced good tablets (weight per tablet, 0.5 gram) but they were not as hard as those made from the preceding two lots.

A fourth lot of the pectin-coated acetylsalicylic acid particles weighing 45 grams was mixed with 45 grams of the Italian citrus pectin, 2 grams of "Cab-O-Sil", M-5 grade, 1 gram magnesium stearate, and 7 grams of potato starch. On compression, fairly good tablets (weight per tablet, 0.4 grams) were produced, but the compression required was considerably greater than for lots 1, 2 or 3.

EXAMPLE 5

A dry mixture was prepared with 200 grams aspirin USP, powdered, 80 mesh, and 200 grams pure citrus pectin, 220 US grade. The mixture was spread out on a polyethylene sheet and sprayed with distilled water, in small increments while turning the mixture over after each successive addition of water, until the material appeared to agglomerate. Any lumps that formed in this operation were crushed. The total weight of the moistened mix was 770 grams. About 370 grams of water were added in the spraying operation. There were handling losses particularly from dusting of the dry starting mixture.

The moistened mix was spread out in a thin layer and placed in a drying oven at 50° C. for about 2 days. The resulting product weighed 390.4 grams, and thus it is probable that most, if not all the water had been evaporated, the lacking 9.6 grams probably constituting the handling losses. The product, which included hard granules, was forced, with some difficulty, through a 16 mesh stainless steel screen by means of a hardwood block. The final granulation was rather coarse, with only a small proportion of fines, and on compression yielded tablets which were reasonably firm, grainy, and fairly glossy.

EXAMPLE 6

A 50:50 mixture (by weight) of aspirin USP, powdered, 80 mesh, and Italian citrus pectin (240 US grade, slow set) was prepared and the mix was gently pressed with a pestil in a mortar to crush any lumps. 20 grams of the mix were added to 180 ml. distilled water and thoroughly stirred, resulting in a very heavy cream. Another 20 grams of the mix were added to the cream and thoroughly mixed therewith, forming a gel which barely dropped off a spatula. The gel was "shorter" than it normally would be for the high pectin concentration attained. The said gel was added to 60 grams of the said mix and thoroughly mixed together, resulting in a rather stiff dough. Another 20 grams of the said aspirin-pectin mix was added to the dough, followed by thorough mixing. The dough became stiffer. 60 grams of the 50:50 aspirin-pectin mix was added and stirred in, resulting in a rubbery material. Finally an additional 100 grams of the 50:50 aspirin-pectin mix was added to the latter material and stirred in. The rubbery lumps that formed were broken up forming a substantially dry, granular product. It was forced through an 8-mesh screen and then a 16-mesh screen by means of a hardwood block. The screened material was spread out in a thin layer and set out in an ambient temperature room equipped with a dehumidifier, for about 1 day. After that, the demoisturized product weighed about 290 grams and appeared dry to the eye and touch. It was calculated to contain at least 10 grams of water, or about 3.4% and perhaps up to 7 or 8% in view of handling losses. The partially demoisturized material compressed well into good tablets (weight per tablet, 0.5 gram) without additives. On dropping these tablets in water, the quick, mushroom growth and disintegration described in Example 3 was not noticeable. The tablets remained solid and surrounded with a gel layer, and swelled gradually, increasing in size.

A portion of the above partially de-moisturized material was mixed with about 1% by weight of magnesium stearate. Compression produced fine, hard tablets (weight per tablet, 0.5 gram) which behaved in water substantially like those without the magnesium stearate.

A further portion, 90 parts by weight, of the above partially de-moisturized material were mixed with 8 parts of potato starch and 2 parts of "Cab-O-Sil", M-5 th grade. The mixture compressed very well and furnished excellent tablets (weight per tablet, 0.5 gram). When dropped in water, they showed substantially the same mushrooming as that described in Example 3 but not quite so pronounced.

EXAMPLE 7

Equal parts by weight of aspirin powder USP, 80 mesh, and Italian citrus pectin (240 US grade, slow set) were mixed together in a mixer at slow speed. After thorough mixing, the stirring was alternately stopped and started, and during the periods of no stirring, the mix was sprayed with small amounts of water in successive steps. Thorough mixing followed each addition of water. To 600 grams of the mix, 400 ml. of distilled water were added in this manner. Toward the final addition of water, the volume of the material had increased considerably, and a noticeable proportion of the material was nodulated into pieces about the size of lentils up to that of peas. The product was spread out in a thin layer and subjected to a drying atmosphere as in Example 6. After about a day, the material was passed through a 16-mesh screen, and the coarser nodules were further ground to pass through this screen. The final mix weighed 635 grams. Thus it contained about 6% water, and perhaps more, taking handling losses into consideration.

Some of the resulting product was tableted without additives. Excellent tablets (weight per tablet, 0.5 gram) were produced.

A second lot of the above moisturized granular product was mixed with 1% magnesium stearate. The mixture did not tablet well. There was capping and disintegration. In view of the hydrophobic nature of magnesium stearate, it may be that for the addition of this chemical the granulation may have been too moist.

A further amount (90 grams) of the above moisturized granulation was thoroughly mixed with 8 grams of potato starch, and 2 grams of "Cab-O-Sil", M-5 th grade. This formulation was compressed into tablets (weight per tablet, 0.5 gram) that were reasonably good, but slightly softer and more friable than is desired.

Tablets of the above three lots when dropped into water behaved substantially like tablets of the respective three lots or portions of Example 6.

EXAMPLE 8

To 360 ml. of water in the bowl of a mixer, were gradually added in successive amounts, a mixture containing 280 grams pure citrus pectin (220 grade) and 280 grams of aspirin powder, 80 mesh, USP, with thorough stirring after each addition. There appeared to be substantially more gelling than was noted in the use of slow set Italian citrus pectin, as in Example 6. The product became dry much sooner and it never became as rubbery as the product prepared in Example 6. After all additions were made, the stirring was continued for about an hour. The mix was kept for about 1 day in an air-tight container and was then stirred in a mixer for about 15 minutes. It was then passed through a 16-mesh screen. The coarser material was ground to pass through the screen. The screened material was spread out in a thin layer and allowed to stand at room temperature in a dehumidified atmosphere for about 2 days. After this, the weight of the material was 557 grams. There had been comparatively small handling losses, and thus the product was apparently quite dry.

Direct compression of the dry granulation provided tablets, 80% of which were of good appearance and reasonably firm, and the remainder (20%) capped and broke. The broken tablets were gently pressed through a 16-mesh screen and the product was re-tableted. Relatively few were broken by capping. The product was too dry for best tabletting results. The tablets (weight per tablet, 0.53 gram) disintegrated well in water, forming piles of particles, with a fair mushroom effect.

A part of the original granulation was screened through a 60-mesh screen. The fines that formed weighed 111.4 grams, and were treated with successive increments of water, the total weight of which was 73.2 grams. After each added increment of about 5 ml. of water, the mixture was thoroughly stirred and lumps that formed were broken up. The final moisturized product was damp, and packed together, but was not slimy or gelatinous. It was kept in an air-tight container for 3 days, and then spread out in a thin layer on a glass tray at room temperature. The coarser part of the 60-mesh screening, weighing about 51.9 grams was combined with the fines treated as described. After a day the mix was weighed and the moisture content was calculated to be about 2%. Tableting was successful. The tablets were of medium hardness and not very smooth. They disintegrated well in water, forming a pile of coarse material with small mushrooming effect.

90 grams of the original granulation of this example, were mixed with 8 grams of potato starch and 2 grams of "Cab-O-Sil", M-5 grade. The powder was thoroughly mixed with a spatula while rubbing down the large lumps of "Cab-O-Sil" agglomerates. 5 ml. of distilled water were added to the resulting powder, in portions of about 1 ml. at a time, with constant mixing and spatulation, until the water was thoroughly distributed. The moisturized powder was kept in a sealed, air-tight container for 2 days to permit water equalization in the mixture. The material tableted very well, and the tablets were quite firm. They disintegrated with ease in water, forming a small pile and giving a fair mushroom effect.

A thorough mixture of 8 grams of potato starch and 2 grams of "Cab-O-Sil", M-5 grade, was prepared, and five successive increments of 1 ml. each of water were distributed in the mix until the powder was smooth, fine and free-running. This moisturized powder was added gradually to 90 grams of the original granulation of Example 8, and the whole was thoroughly mixed. The resulting material was kept for 2 days in a sealed container, and thereafter tableted. It tableted very well, the tablets were firm, and there was no capping. When dropped into water, the tablets disintegrated very well, forming a small pile with fair mushrooming.

EXAMPLE 9

| | |
|---|---|
| Potato starch | 80 grams |
| "Cab-O-Sil", M-5 | 20 grams |
| Water | 50 grams |

These three ingredients were thoroughly mixed, and spatulated to break up any small lumps in the mix. The resultant material was a fine powder which had a dry appearance. It was distributed in a mixture of:

| | |
|---|---|
| Pure citrus pectin (220 US grade) | 450 grams |
| Aspirin Powder, 80 mesh, USP | 450 grams |

One-half of the final mix was tableted directly. Fine, firm tablets (weight per tablet, slightly over 0.5 gram) were produced. The tablets were permitted to dry in the air to prevent hydrolysis of the aspirin.

The other half of the above final mix was kept in a closed container for about 24 hours to give the moisture a chance to distribute itself over all of the ingredients by isothermal distillation. The pectin particles under such conditions pick up water and are somewhat softened thereby. Excellent tablets were produced from the mixture thus aged. They were fairly hard and semi-glossy, and disintegrated rapidly when dropped in water, giving the mushroom effect described in Example 3. The tablets obtained from the first half of the above final mix also produced this effect.

The ingredients of the above formula were brought together in the same proportions and by the same procedure but 40-mesh aspirin powder was substituted for the 80-mesh. One-half of this mix was immediately tableted. The other half was tableted after water-equalization (as above described) for a day. The tablets (weight per tablet, about 0.6 gram) were firmer and heavier than those prepared with the 80-mesh aspirin powder, but they produced a fine mushroom effect in water, with rapid disintegration, and showing more granular material.

A fresh batch of ingredients of the above formula was prepared but aspirin powder containing 50 parts by weight of 40-mesh and 50 parts by weight of 80-mesh aspirin powder was used instead of all 80-mesh. The granulation tableted well and the tablets (weight per tablet, 0.6 gram) were very firm and heavy. They disintegrated rapidly in water, giving the mushroom effect. This granulation when dry, or de-moisturized too much, does not tablet well.

EXAMPLE 10

A mixture was prepared from 50 grams pure citrus pectin (220 US grade) and 500 grams aspirin, 40-mesh. This mixture was added bit by bit to 1000 ml. of water while stirring. There was substantially no clumping of the pectin. Because of the presence of the relatively large proportion of aspirin, no actual gelling occurred, but a slimy paste was formed. To this paste was added gradually 450 grams of the same variety of pectin which was thoroughly kneaded in the mix. Soft lumps were crushed, and ultimately a fairly uniform, nodulated, free-flowing product was formed in which individual aspirin particles were coated with pectin. This material was spread out on a paper sheet to dry and was turned over with a spatula now and then, while crushing the lumps that formed. The material was finally passed through a 16-mesh screen. The water retention was calculated to be about 11.5% in addition to the original weight of aspirin and pectin. Direct tableting was relatively unsuccessful. The tablets were friable, or on more compression, material stuck to the dies. This indicated that the moisture content was too high. After further drying to a moisture content of about 5 to 6% in addition to the original weight of aspirin and pectin, fairly firm tablets (weight per tablet, 0.5 gram) were produced. They disintegrated quickly in water.

EXAMPLE 11.

| | |
|---|---|
| Potato starch | 8 grams |
| "Cab-O-Sil", M-5 | 2 grams |

These two ingredients were thoroughly mixed, and 5 ml. water were added in successive amounts, or successive increments, of 1 ml. each, with final spatulation to eliminate any small lumps.

A mixture was then prepared of:

| | |
|---|---|
| Aspirin powder, 80-mesh, USP | 22.5 grams |
| Pure citrus pectin (220 US grade) | 67.5 grams |

The above two mixtures were mixed thoroughly together. The resulting product was a fine, dry-appearing, light tan powder. After water equalization for one day in a closed container, the pourable powder was successfully tableted. The excellent, firm tablets disintegrated quickly in water with huge mushroom-like formation.

EXAMPLE 12

A composition was prepared with the following ingredients by the method employed in Example 11:

| | |
|---|---|
| Potato starch | 5 grams |
| "Cab-O-Sil", M-5 | 5 grams |
| Water | 10 grams |
| Aspirin powder, 80-mesh, USP | 9 grams |
| Pure citrus pectin (220 US grade) | 81 grams |

Tablets made with this composition were not as firm as those of Example 11, but they were good tablets which disintegrated in water with hugh mushroom formation.

EXAMPLE 13

A composition was prepared with the following ingredients by the method employed in Example 11:

| | |
|---|---|
| Potato starch | 8 grams |
| "Cab-O-Sil", M-5 | 2 grams |
| Water | 5 grams |
| Aspirin powder, 80-mesh, USP | 67.5 grams |
| Pure citrus pectin (220 US grade) | 22.5 grams |

Excellent, firm tablets were made with this composition. They disintegrated quickly in water but the mushroom effect was relatively less noticeable.

EXAMPLE 14

A composition was prepared with the following ingredients by the method employed in Example 11:

| | |
|---|---|
| Potato starch | 8 grams |
| "Cab-O-Sil", M-5 | 2 grams |
| Water | 5 grams |
| Aspirin powder, 80-mesh, USP | 81 grams |
| Pure citrus pectin (220 US grade) | 9 grams |

Excellent, firm tablets were made with this composition. They disintegrated quickly in water but jelly matter that was formed around the tablets was relatively less noticeable.

EXAMPLE 15

A composition was prepared with the following ingredients by the method employed in Example 11:

| | |
|---|---|
| Potato starch | 8 grams |
| "Cab-O-Sil", M-5 | 2 grams |
| Water | 5 grams |
| Aspirin powder, 80-mesh, USP | 45 grams |
| Italian citrus pectin, slow set, 240 US grade | 45 grams |

Good but fairly hard tablets were made with this composition. In water, these tablets slowly swelled in size. They tended to keep their form, showed no disintegration and none of the aforementioned mushroom effect.

EXAMPLE 16

To produce tablets which would be partially slow and partially fast acting, the following formulation was used in preparing such tablets by the method of Example 11:

| | |
|---|---|
| Final granulation of Example 6 | 45 grams |
| Aspirin powder, 80-mesh, USP | 22.5 grams |
| Pure citrus pectin (220 US grade) | 22.5 grams |
| Potato starch | 8 grams |
| "Cab-O-Sil", M-5 | 2 grams |
| Water | 30 grams |

Very good tablets of medium firmness were made with this formulation. They disintegrated readily in water, with swelling; showed good gelling and relatively less of a mushroom effect; and during such observations the original granules of Example 6 contained therein were clearly visible.

EXAMPLE 17

Three varieties of Swiss apple pectin of different degrees of demethoxylation were incorporated in three separate compositions (noted below) which were used in preparing tablets by the method of Example 11:

| | | |
|---|---|---|
| (a) | Aspirin powder, 80-mesh, USP | 45 grams |
| | Swiss apple pectin, 25–28% D.M. | 45 grams |
| | Potato starch | 8 grams |
| | "Cab-O-Sil", M-5 | 2 grams |
| | Water | 5 grams |
| (b) | Aspirin powder, 80-mesh, USP | 45 grams |
| | Swiss apple pectin, 35–38% D.M. | 45 grams |
| | Potato starch | 8 grams |
| | "Cab-O-Sil", M-5 | 2 grams |
| | Water | 5 grams |
| (c) | Aspirin powder, 80-mesh, USP | 45 grams |
| | Swiss apple pectin, 40–43% D.M. | 45 grams |
| | Potato starch | 8 grams |
| | "Cab-O-Sil", M-5 | 2 grams |
| | Water | 5 grams |

It is customary in the trade in referring to low methoxyl pectins to designate them by a percentage figure followed by the letters D.M. For instance, in Example 17(a), reference is made to Swiss apple pectin 25–28% D.M. By this is meant that this particular grade of pectin contains 25–28% of the theoretically possible amount of methoxyl groups of pectin. If the theoretically possible amount is 16.34%, this particular apple pectin may contain 25 to 28% of 16.34%, or a total of about 4.0 to 4.5% methoxyl groups.

Each of the above compositions of example 17 tableted well, forming fine, firm, medium-hard tablets. They tended to keep their form in water though they swelled noticeably, and the outer zones became gelatinous. The Swiss low-methoxyl apple pectins thus behaved substantially like Italian slow-set pectin and are considered useful in preparing delayed action tablets.

EXAMPLE 18

APC compound tablets (Aspirin-Phenacetin-Caffeine).

| | |
|---|---|
| Medicaments | 90 grams (45%) |
| Pectin (Mutual 220 US grade) | 90 grams (45%) |
| C-O-S (M-5) | 4 grams ( 2%) |
| Starch (potato starch) | 16 grams ( 8%) |
| Water | 10 grams |

The water evaporates and is not a part of the finished tablet. The medicaments in the above composition are proportioned as follows:

| | | |
|---|---|---|
| Aspirin | 48.4 grams approximately | 53.85% |
| Phenacetin | 34.6 " | 38.85% |
| Caffeine | 7.0 " | 7.30% |

The starch and C-O-S ("Cab-O-Sil") are mixed, the water is then incorporated while stirring. Any small lumps that form are crushed by spatulation. Then the mixture of pectin and medicaments is incorporated with the starch-"Cab-O-Sil"-water, pourable powder. The completed mix is kept in a closed jar for about 18 hours to permit isothermal distillation of the water, and moisture pick-up by the pectin. The composition is then tableted. Very good tablets are formed. In water, the tablets disintegrate very rapidly, each forming a high mushroom-like gel or jelly-like mass in which undissolved particles of the medicament are distributed.

EXAMPLE 19

| | |
|---|---|
| Aspirin (powder, 40 mesh) | 45 grams |
| Kelcoloid HVF (fibrous, 80 mesh) (An ester of alginic acid: propylene glycol ester of alginic acid) (2% in water yields a viscosity of 7000 cps) | 45 grams |
| Starch (potato) | 8 grams |
| "Cab-O-Sil", M-5 | 2 grams |
| Water | 5 grams |

The water is added to the "Cab-O-Sil" drop by drop; then the starch is mixed in; small lumps that form are crushed by spatulation; the mixture of Kelcoloid and aspirin is added and mixed in. The resulting mix is spatulated and finally homogenized in a mortar without grinding, or made more uniform by placing it in a closed jar and by rolling the jar on a roller mill. After 18 hours confinement in the jar to permit isothermal distillation to equalize (uniformly distribute) the moisture content, and to permit water pick-up by the Kelcoloid, the product is converted into tablets. Good smooth tablets are produced.

EXAMPLE 20

| | |
|---|---|
| Aspirin (powder, 40 mesh) | 75 grams |
| Kelcosol (sodium alginate powder, 80 mesh. 2% in water yields a viscosity of 14000 centipoises) | 15 grams |
| Starch (potato) | 8 grams |
| "Cab-O-Sil", M-5 | 2 grams |
| Water | 5 grams |

Mixing of these ingredients and the general treatment of the composition are carried out substantially as in Example 19. After about 20 hours for isothermal water equalization, the mix provides excellent tablets which are glossy and firm without being too hard. They disintegrate rapidly in water with formation of a large, mushroom-like, gel mass.

EXAMPLE 21

A mix is prepared similar to that in Example 20, except that instead of the Kelcosol, there is substituted 10 grams of Keltone, a powder of about 150 mesh, consisting of sodium alginate that yields a 2% water solution with a viscosity of 3500 centipoises; and aspirin (40 mesh powder) is increased to 80 grams. After 3 hours of isothermal water equalization in a closed jar, the mix provides tablets that are less hard and glossy but entirely satisfactory. When placed in water, they surround themselves with a large gel layer, and the tablets eventually split into two layers horizontally. Subsequently, they disintegrate into gel or jelly-like gobs in which aspirin particles can be seen.

In tablets prepared as illustrated above, a satisfactory mix for preparing them is one containing approximately 8 parts by weight of starch, about 2 parts by weight of "Cab-O-Sil", about 5 parts to about 10 parts by weight of water, and about 90 parts by weight of a mixture of aspirin and pectin. The latter mixture contains aspirin substantially in the range of 9 to 81 parts, the balance of the above 90 parts being pectin. In such tablet mix, the ratio of starch to "Cab-O-Sil" may be varied somewhat, if desired, up to equal parts by weight. In general, the higher the percentage of pectin in the total tablet mix, the greater should be the proportion of "Cab-O-Sil" in the said ratio of starch to "Cab-O-Sil".

In the use of water in the various examples hereinabove, it may be either in liquid or solid form. When liquid water is employed, the temperature thereof is preferably at ambient room temperature, but somewhat elevated temperature may be used, so long as the hydrolysis of acetylsalicylic acid is substantially avoided.

What is claimed is:

1. A method of providing a pharmaceutical product, which method comprises preparing an initial mix of substantially equal parts by weight of aspirin and pectin, spraying water on the solid mix in successive small increments while agitating the said mix, the amount of water thus added being above 10% but below that required to change the mix to a lumpy paste, subjecting the moisturized mix to isothermal distillation drying conditions until the water content is reduced to the approximate range of 2 to 10% by weight in addition to the natural moisture content of the pectin used, and compressing the resulting material into tablets.

2. A pharmaceutical tablet with improved rapidity of disintegration, in water, into a mushroom-like gel mass produced in accordance with claim 1.

3. A method of providing a pharmaceutical product, which method comprises preparing an initial mix of substantially equal parts by weight of aspirin and pectin, mixing a part of said initial mix and water to form a cream-like product, adding to the latter water-treated mix, with stirring, successive increments of the said initial mix until on further stirring a dry-appearing granular product is obtained, subjecting the granular material to isothermal distillation drying conditions until the water content is reduced to the approximate range of 2 to 10% by weight based on the original total mix of the aspirin and pectin and compressing the resulting material to form tablets.

4. A pharmaceutical tablet with improved rapidity of disintegration, in water, into a mushroom-like gel mass produced in accordance with claim 1.

5. A method comprising mixing with substantially 90 parts by weight of a mixture containing substantially 9 parts to 81 parts by weight of aspirin and substantially 81 parts to 9 parts by weight of pectin, a mixture of substantially 8 parts by weight of starch and 2 parts by weight of colloidal, pyrogenic silica, which latter mixture is moistened with substantially 5 parts by weight of water based on the total mix; and placing the resulting mix in a closed chamber to promote equal distribution of the water in the said latter mix by isothermal distillation, prior to compressing the resulting mixture into tablets.

6. A pharmaceutical tablet with improved rapidity of disintegration in water, produced in accordance with claim 5.

7. A method comprising mixing together substantially 80 parts by weight of starch, substantially 20 parts by weight of colloidal, pyrogenic silica, and substantially 50 parts by weight of water; breaking up lumps in the mix to form a uniform dry-appearing powder, mixing the said powder and substantially 900 parts by weight of a mixture containing substantially equal parts by weight of aspirin and pectin, and placing the resulting material in a closed container to permit substantially uniform distribution of water by isothermal distillation and to thereby soften the surfaces of individual pectin particles in said material, prior to compressing the resulting mixture into tablets.

8. A pharmaceutical tablet with improved rapidity of disintegration in water, produced in accordance with claim 7.

* * * * *